United States Patent [19]

Machell

[11] Patent Number: 4,562,265

[45] Date of Patent: Dec. 31, 1985

[54] METHOD FOR PRODUCING A DI-ACETAL OF SORBITOL AND AN AROMATIC ALDEHYDE

[75] Inventor: Greville Machell, Spartanburg, S.C.

[73] Assignee: Milliken Research Corporation, Spartanburg, S.C.

[21] Appl. No.: 135,017

[22] Filed: Mar. 28, 1980

Related U.S. Application Data

[63] Continuation-in-part of Ser. No. 83,895, Oct. 11, 1979, abandoned, which is a continuation of Ser. No. 967,024, Dec. 6, 1978, abandoned.

[51] Int. Cl.$^4$ .............................................. C07D 323/04
[52] U.S. Cl. ..................................................... 549/364
[58] Field of Search ....................... 260/340.7; 549/364

[56] References Cited

U.S. PATENT DOCUMENTS

| | | | |
|---|---|---|---|
| 3,721,682 | 3/1973 | Murai et al. | 260/340.7 |
| 4,131,612 | 12/1978 | Uchiyama et al. | 260/340.7 |
| 4,267,110 | 5/1981 | Uchiyama | 260/340.7 |

FOREIGN PATENT DOCUMENTS

| | | | |
|---|---|---|---|
| 0185288 | 11/1982 | Japan | 549/364 |
| 0180488 | 10/1983 | Japan | 549/364 |
| WO81/03331 | 11/1981 | PCT Int'l Appl. | 549/364 |

OTHER PUBLICATIONS

C.A. 53:21678c (1959).
Wolfe et al., Journ. Amer. Chem. Soc. 64 (1942), pp. 1493–1497.
C.A. 47:3235g (1952).
C.A. 75:P6245d (1971).
Chem. Abstract 53:21678f (1959).

*Primary Examiner*—Ethel G. Love
*Attorney, Agent, or Firm*—H. William Petry; Terry T. Moyer

[57] ABSTRACT

A method is provided for producing a di-acetal of sorbitol and an aromatic aldehyde wherein an aqueous solution containing a catalytic amount of a mineral acid and sorbitol is formed. Thereafter, an effective amount of an aromatic aldehyde such as benzaldehyde is incrementally admixed into the homogeneous aqueous admixture containing the sorbitol at a rate sufficient to allow a substantially spontaneous reaction to occur between the D-sorbitol and aromatic aldehyde; thus, forming an aqueous slurry containing crude di-acetal, e.g., dibenzylidene sorbitol. The amount of aromatic aldehyde employed is that amount sufficient to provide a molar ratio of D-sorbitol to aromatic aldehyde of from about 1:0.75 to about 1:1.75. Thereafter, the aqueous slurry is neutralized, and crude di-acetal is removed from the liquid phase and washed with water to remove mono-acetal impurities, e.g., monobenzylidene sorbitol. The washed di-acetal may then be dried to provide dried di-acetal, and the dried di-acetal may be further purified by washing with a relatively non-polar solvent.

12 Claims, No Drawings

METHOD FOR PRODUCING A DI-ACETAL OF SORBITOL AND AN AROMATIC ALDEHYDE

This invention relates to di-acetals of sorbitol and an aromatic aldehyde, e.g., dibenzylidene sorbitol. In one aspect it relates to an improved method for the manufacture of di-acetals of sorbitol and an aromatic aldehyde.

Di-acetals of sorbitol and aromatic aldehydes, such as, for instance, dibenzylidene sorbitol, have heretofore been known as polymer additives for imparting unique properties to certain polymers. For example, dibenzylidene sorbitol has been employed as a clarifying agent for polyolefins, especially polyethylene and polypropylene to improve the transparency of films made from such polyolefins. While the use of dibenzylidene sorbitol for polymer additives has shown much promise and utility, problems have nevertheless been encountered in providing economical commercial methods for the manufacture of dibenzylidene sorbitol having a degree of purity sufficient to justify its manufacture.

Therefore, an object of the present invention is to provide an improved method for the manufacture of di-acetals such as dibenzylidene sorbitol by the condensation of sorbitol and aromatic aldehydes.

Another object of the invention is to provide an economical commercially feasible method for producing di-acetals of sorbitol and an aromatic aldehyde, such as dibenzylidene sorbitol, for use as polymer additives.

These and other objects, advantages, and features of the present invention will be apparent to those skilled in the art from a reading of the following detailed disclosure.

According to the present invention, I have discovered a method for producing di-acetals of sorbitol and an aromatic aldehyde which comprises admixing an effective amount of D-sorbitol into an aqueous solution containing a catalytic amount of a mineral acid so as to form a homogeneous aqueous admixture containing the mineral acid. Thereafter, an effective amount of an aromatic aldehyde is incrementally admixed into the homogeneous aqueous admixture containing the D-sorbitol at a rate sufficient to allow a substantially spontaneous reaction between the D-sorbitol and the aromatic aldehyde, thereby resulting in an aqueous slurry containing crude di-acetal. The aqueous slurry of the crude di-acetal is then neutralized and the crude di-acetal separated from the liquid phase of the neutralized aqueous slurry. The crude di-acetal is then washed with water to remove mono-acetal impurities present in the crude di-acetal product. The washed di-acetal is then dried to remove substantially all of the residual water and provide a purified, dry di-acetal product.

It should be appreciated with regard to the di-acetals of sorbitol and aromatic aldehyde made according to the process of the present invention that what is intended is the disubstituted compound, e.g., the sorbitol component will be substituted with two molecules of aromatic aldehyde, rather than one or three molecules. Thus, in the case of benzaldehyde, the condensation product will be dibenzylidene sorbitol rather than monobenzylidene sorbitol or tribenzylidene sorbitol, which later compounds may have other utilities but are considered to be, and therefore are defined as "impurities" insofar as the present invention is concerned. Other examples of "di-acetals", as the term is defined according to the present invention, include, e.g., di(p-chlorobenzylidene) sorbitol, di(m-chlorobenzylidene) sorbitol, di(methylbenzylidene) sorbitol, etc.

It has been found that a mineral acid should be provided in the aqueous solution to which the D-sorbitol is added. The acid should be present in a catalytic amount which can vary widely and which may depend to a certain extent on the acid strength of the particular acid employed. Generally a catalytic amount is from about 10 to 75 weight percent, preferably from about 15 to 60 weight percent or even 30 to 60 weight percent, based on the total amount of water present in the reaction mixture. The preferred mineral acids may be hydrochloric acid and sulphuric acid, although others, such as orthophosphoric acid may be employed. When the acid employed is hydrochloric, the preferred acid concentration has been found to be from about 10 to 25 weight percent, preferably 10 to 20 weight percent. When sulphuric acid is used the preferred concentration may be from about 30 to 60 weight percent, preferably 35 to 50 weight percent.

The amount of D-sorbitol admixed with the aqueous solution of the mineral acid to form a homogeneous aqueous admixture containing the mineral acid can vary widely. However, the amount of D-sorbitol employed should not exceed the solubility characteristics of D-sorbitol in the aqueous solution of the mineral acid at the temperature at which the reaction between the D-sorbitol and aromatic aldehyde is carried out.

Once the desired amount of D-sorbitol has been incorporated into the aqueous solution of the mineral acid containing the amount of mineral acid as heretofore specified, an aromatic aldehyde is incrementally added to the homogeneous aqueous admixture containing the D-sorbitol at a rate sufficient to allow a substantially spontaneous reaction to occur between the D-sorbitol and the aromatic aldehyde. Such incremental addition is generally achieved by very slowly adding the aromatic aldehyde to the aqueous admixture while maintaining the aqueous admixture under agitation. Further, the amount of aromatic aldehyde added to the aqueous admixture containing the D-sorbitol is that amount sufficient to provide a molar ratio of D-sorbitol to aromatic aldehyde of from about 1:0.75 to about 1:1.75, preferably about 1:1 to about 1:1.5, or even about 1:1.25 to about 1:1.75.

A wide variety of aromatic aldehydes and mixtures of aromatic aldehydes may be employed in the process of the invention. Examples of such aromatic aldehydes include benzaldehyde, ortho-, para- and meta-tolualdehyde, anisaldehyde and substituted benzaldehydes having one to three substituents and wherein the substituents are selected from lower alkyl, methoxy, mono- and di-alkylasino, amino, nitro or halogen. Preferred aromatic aldehydes include benzaldehyde, meta- and para-chlorobenzaldehyde, meta- and para-bromobenzaldehyde and meta- and para-tolualdehyde.

The reaction between the D-sorbitol and aromatic aldehyde to form the desired condensation product can be carried out at various temperatures. In the case of benzaldehyde, for instance, it has been determined that such reaction may be desirably carried out at ambient or room temperatures. In the case of other aldehydes temperatures above or even below ambient or room temperatures may be more suitable.

Once the aromatic aldehyde has been added to the aqueous admixture containing the D-sorbitol and the mineral acid and an aqueous slurry results from the formation of the di-acetal, the aqueous slurry is neutralized with an alkali substance, such as sodium hydroxide, potassium hydroxide, sodium bicarbonate and the like. The amount of alkali material employed may vary widely. It may be desirable in some applications that the amount of alkaline material employed be slightly in excess of the amount required to neutralize the aqueous slurry admixture, although large excesses of alkali should be avoided.

After the aqueous slurry admixture has been neutralized, the crude di-acetal which is the solid material of the aqueous slurry admixture containing minor amounts of mono-acetal impurities, such as monobenzylidene sorbitol, is separated from the liquid phase of the neutralized aqueous slurry admixture. It may be desirable to include the step of washing the crude di-acetal with cool water to remove any residual salts formed as a result of the neutralization of the aqueous slurry and excess alkali material present in the wet, crude di-acetal product. When washing the wet, crude di-acetal product with cool water, the temperature of the water can vary widely. However, it is believed that best results will be obtained when the water is maintained at a temperature of from about 20° C. to about 40° C. The separated, wet, crude condensation product may then be washed again with warm water to remove the mono-acetal impurities. The temperature of the water employed to wash the crude di-acetal product to remove mono-acetal impurities can vary widely.

The washed product substantially free of the mono-acetal impurities may thereafter be dried to remove residual water and provide purified, substantially dried di-acetal product. Drying can be accomplished by any conventional method known in the art, such as use of a vacuum oven, convection heat and the like. The drying temperature is not critical provided such is sufficient to effectively dry the material but not decompose same. Subsequent to drying the purified di-acetal product may be even further purified by extracting same with a relatively non-polar solvent as will be described hereinbelow in greater detail.

It may be desirable to operate the method for producing di-acetal in a continuous or semi-continuous method. In such instance, it is desirable that the crude di-acetal product be removed from the liquid phase of the aqueous slurry prior to neutralization so that the recovered liquid phase can be recycled or employed for further makeup of the initial aqueous solution of the mineral acid and the D-sorbitol. In such instance, the crude solid di-acetal product separated from the liquid phase can be neutralized using an aqueous solution of an alkali material, such as those set forth hereinabove, and thereafter the neutralized product may be washed using warm water or a combination of cool water and warm water as recited above.

The separation of the crude di-acetal product from the aqueous slurry containing same can be accomplished by any suitable means well known in the art, such as filtration, centrifuging, and the like.

In order to further illustrate the present invention, the following examples are given. However, these examples are for illustrative purposes only and are not to be construed as unduly limiting the scope of the subject invention as set forth in the claims hereafter.

EXAMPLES

Procedure A

This procedure was employed for Examples 1–5, 10, 12 and 13 shown in Tables 1 and 2. A 70 percent aqueous solution of sorbitol (135 grams, 0.5 mole), the appropriate amount of benzaldehyde to give the molar ratio of benzaldehyde to sorbitol shown in Tables 1 and 2, and the designated aqueous mineral acid solution (200 grams) of the concentration indicated, were placed in a 1-liter vessel fitted with a Teflon paddle stirrer. This reaction mixture was stirred at about 25° C. until the viscosity had risen to the point where stirring was no longer effective. The acid was then neutralized to an extent of about 98 percent with a 10 percent aqueous solution of sodium hydroxide, and the reaction mixture finally brought to a pH of about 8 with 10 percent sodium carbonate. The white, solid product was filtered, washed thoroughly with water, and dried at 95° C. in a convection oven.

High-performance liquid chromatography was then used to determine the ratio of dibenzylidene sorbitol (DBS) to tribenzylidene sorbitol (TBS) in the product.

Procedure B

This procedure was similar to Procedure A except that the stated molar amount of benzaldehyde was added dropwise to the reaction mixture over a period of about 4 hours in the following manner: first hour, 50 percent; second hour, 25 percent; third hour, 15 percent; fourth hour, 10 percent. The reaction was then continued for a short time to achieve the desired high viscosity, neutralized, and the product isolated as described under Procedure A.

EXAMPLES 1–5

In Example 1 Procedure A was employed using a mole ratio of benzaldehyde to sorbitol that would be theoretically required to produce DBS (2:1 mole ratio). The product obtained actually showed a DBS/TBS ratio of 75:25. By reducing the mole ratio of benzaldehyde to sorbitol, firstly to 1.5:1, and then to 1:1, in Examples 2 and 3 respectively, the DBS/TBS ratio in the product steadily increased to 83/17. A similar effect was observed in Examples 4 and 5, where a higher acid concentration was used. The results are summarized in Table 1.

EXAMPLES 6–9

In Examples 6–9 Procedure B was employed rather than Procedure A and a lower mole ratio of benzaldehyde to sorbitol was also employed resulting in a further increase in the DBS/TBS ratio, reaching a maximum ratio of 91:9 in Example 9. The results are summarized in Table 1.

TABLE 1

| | | Hydrochloric Acid Catalyst | | | | | |
| --- | --- | --- | --- | --- | --- | --- | --- |
| Example Number | Procedure | Mole Ratio Benzaldehyde to Sorbitol | Acid Concentration | Product Yield Gram | %* | Normalized DBS:TBS In Product | Melting Point °C. |
| 1 | A | 2:1 | 15% | 110 | 64 | 75:25 | 185–200 |
| 2 | A | 1.5:1 | 15% | 75 | 58 | 80:20 | 183–195 |
| 3 | A | 1:1 | 15% | 48 | 55 | 83:17 | 192–200 |

TABLE 1-continued

| | | Hydrochloric Acid Catalyst | | | | | |
|---|---|---|---|---|---|---|---|
| Example Number | Procedure | Mole Ratio Benzaldehyde to Sorbitol | Acid Concentration | Product Yield Gram | %* | Normalized DBS:TBS In Product | Melting Point °C. |
| 4 | A | 2:1 | 18% | 108 | 62 | 83:17 | 194–206 |
| 5 | A | 1.25:1 | 18% | 69 | 64 | 85:15 | 203–210 |
| 6 | B | 1.75:1 | 18% | 101 | 66 | 83:17 | 194–200 |
| 7 | B | 1.5:1 | 18% | 89 | 68 | 84:16 | 194–204 |
| 8 | B | 1.25:1 | 18% | 76 | 69 | 88:12 | 200–207 |
| 9 | B | 0.75:1 | 18% | 42 | 63 | 91:9 | 202–215 |

*Yield based on the amount of benzaldehyde employed.

EXAMPLES 10–17

In Examples 10–17 generally similar effects were observed with a sulfuric acid catalyst. The results are summarized in Table 2, where the higher DBS/TBS ratio of 94/6 is observed in Example 17. Examples 10–17 and Table 2 also illustrate that the percentage yield of product, based on the benzaldehyde employed, rose very significantly as the mole ratio of benzaldehyde to sorbitol is reduced. This is particularly illustrated by comparing Examples 12 and 16 with a 40 percent acid concentration.

Although the melting point of a mixture product tended to be broad and somewhat erratic, it was clear from the results in Tables 1 and 2 that as the DBS/TBS ratio rose significantly, the melting point of the product also tended to rise as would be expected. Again, a comparison of Examples 12 and 16 shows this effect clearly.

Although the improvement of the DBS/TBS ratio as shown in Tables 1 and 2 is of great utility, there may still be a need in certain commercial applications for a product containing an even higher proportion of the DBS component. According to U.S. Pat. No. 4,131,612, a crude DBS product, containing as impurities TBS and other compounds, may be purified by extracting it with a lower aliphatic alcohol, such as methanol, at elevated temperatures. This procedure described in the patent using methanol was applied to the product of Example 17 in Table 2, with the result shown in Table 3. It is seen that the content of DBS in the product actually declined, rather than increasing as would have been expected from the teachings of the abovementioned patent.

According to the present invention all or even a portion of the TBS present in a di-acetal/tri-acetal product may be removed to increase its di-acetal content by employing a relatively non-polar solvent. In Table 3 are also shown the results of extracting DBS/TBS products with relatively non-polar solvents, viz: toluene and 1,1,1-trichloroethane. A liquid-to-solid ratio of 10:1 was employed as in the case of methanol described above. significant increase in the DBS content was achieved, especially in the case of 1,1,1-trichlorethane. The recovery of desired product was also very high. In the case of the 1,1,1-trichlorethane, the liquid extract was concentrated to remove the solvent leaving a residue with DBS/TBS ratio of 8/92.

TABLE 3

| Solvent | Extraction Conditions | DBS:TBS Ratio Initial | Final | Recovery |
|---|---|---|---|---|
| Methanol | 1 Extraction ~60° C. | 94:6 | 93:7 | ~90% |
| Toluene | 3 Extractions ~80° C. | 92:8 | 95:5 | ~85% |
| 1,1,1-Trichloro-ethane | 3 Extractions ~70° C. | 92:8 | 98:2 | ~90% |

EXAMPLE 18

A 70% aqueous D-sorbitol solution (52 grams, 0.2 mole sorbitol) and 48% sulfuric acid (87.1 grams) were placed in a flask with stirrer. Benzaldehyde (31.5 grams, 0.3 mole) was then added dropwise with vigorous stirring over a period of 1 hour and 45 minutes. During the addition, the temperature of the reaction mixture rose from 24° to 28° C., and a pale yellow solid was formed. Continued stirring of the slurry for a further 1 hour and 30 minutes. Poured the contents of the flask into 8% aqueous sodium hydroxide with vigorous stirring to neutralize the acid. Then filtered off the solid, and washed it with cold water to a pH of 5.5. Slurried the solid product in water at 90° C. for 30 minutes, then filtered, and washed the material with more hot water. Dried the product in a vacuum oven to constant weight. Yield: 42 grams (78% yield calculated as dibenzylidene sorbitol, and based on the weight of benzaldehyde employed.) The melting point of the off-white powder was 197°–202° C., versus the literature melting point for dibenzylidene sorbitol of 224° C. Elemental analysis

TABLE 2

| | | Sulfuric Acid Catalyst | | | | | |
|---|---|---|---|---|---|---|---|
| Experiment | Procedure | Mole Ratio Benzaldehyde to Sorbitol | Acid Concentration | Product Yield Gram | %* | Normalized DBS:TBS In Product | Melting Point °C. |
| 10 | A | 2:1 | 36% | 111 | 64 | 79/21 | 189–197 |
| 11 | B | 1:1 | 36% | 64 | 71 | 91/9 | 198–206 |
| 12 | A | 2:1 | 40% | 112 | 65 | 80/20 | 190–198 |
| 13 | A | 1.25:1 | 40% | 82 | 75 | 86/14 | 205–214 |
| 14 | B | 1.25:1 | 40% | 85 | 77 | 92/8 | 201–209 |
| 15 | B | 1.25:1 | 40% | 84 | 76 | 91/9 | 192–202 |
| 16 | B | 1:1 | 40% | 73 | 83 | 93/7 | 212–216 |
| 17 | B | 1:1 | 45% | 70 | 78 | 94/6 | 215–221 |

*Yield based on the amount of benzaldehyde employed.
NOTE:
Experiments 14 and 15 are duplicates.

gave: C, 68.7; H, 6.05%. (Calculated for $C_{20}H_{22}O_6$: C, 67.0; H, 6.2%.)

EXAMPLE 19

The procedure used was essentially similar to that of Example 18, except that the amount of benzaldehyde was increased (41 grams, 0.39 mole). In this case, the yield of product was 50.8 grams (74% based on the benzaldehyde), but the melting point was lower, viz: 175°–179° C. (Found: C, 69.1; H, 6.0)

EXAMPLE 20

Following a similar procedure to Example 18, but with a reduced amount of benzaldehyde (21.2 grams, 0.2 mole) the yield of solid product was 25.2 grams (70% based on the benzaldehyde). The melting point of this material was again lower: 173°–177° C. Found: C, 67.5; H, 5.8).

EXAMPLE 21

Again repeated the procedure of Example 18, but lowered the concentration of the sulfuric acid from 48% to 32% by weight. After completion of the benzaldehyde addition and subsequent stirring period, there was relatively little solid present. Heated the reaction mixture to 70° C. for 1 hour, then cooled overnight, whereupon the reaction mass solidified. On working up the reaction as described there was obtained: 36.1 grams of product (52% yield on the benzaldehyde); melting point 170°–175° C. (Found: C, 68.9; H, 6.2).

The above melting point data provided in Examples 18 through 21 is believed to show the improved purity of dibenzylidene sorbitol employing the concept of the present invention wherein the amount of sorbitol to benzaldehyde is maintained in the specified mole ratio and the benzaldehyde is contacted with the D-sorbitol in such a manner as to allow such reactants to react substantially simultaneously, thus preventing the formation of undesired side products.

That which is claimed is:

1. A method for producing a di-acetal of sorbitol and an aromatic aldehyde which comprises: admixing an effective amount of D-sorbitol into an aqueous solution of a mineral acid so as to form a homogeneous aqueous admixture containing a catalytic amount of said mineral acid; incrementally admixing an effective amount of an aromatic aldehyde into said homogeneous aqueous admixture at a rate sufficient to allow a substantially spontaneous reaction with said D-sorbitol so as to form an aqueous slurry containing crude di-acetal product, said effective amount of aromatic aldehyde, being that amount sufficient to provide a molar ratio of D-sorbitol to aromatic aldehyde of from about 1:.75 to about 1:1.75; neutralizing the aqueous slurry admixture; separating said crude di-acetal product from the liquid phase of the neutralized aqueous slurry; washing the separated crude di-acetal product with water to remove mono-acetal impurities present in said crude di-acetal product; drying the washed di-acetal product to remove substantially all of the residual water; and recovering purified, substantially dry di-acetal product.

2. The method of claim 1 wherein said aromatic aldehyde is selected from benzaldehyde, ortho-, para- and meta-tolualdehyde, anisaldehyde and substituted benzaldehydes having 1 to 3 substituents in their benzene nucleus wherein said substituents are selected from lower alkyl having fewer than five carbon atoms, methoxy, mono- and di-alkylamino, nitro and halogen.

3. The process of claim 2 wherein said aromatic aldehyde is selected from benzaldehyde, meta- and para-tolualdehyde, meta- and para-chlorobenzaldehyde, and meta- and para-bromobenzaldehyde.

4. The method of claim 1 which further includes the step of washing said separated crude di-acetal in two separate steps, in a first step with an effective amount of water maintained at a temperature of from about 20° C. to about 40° C. to remove any residual salts formed as a result of the neutralization of said aqueous slurry and in a second step at a higher temperature to remove other mono-acetal impurities present in said crude di-acetal.

5. The method of claim 1 wherein said acid is hydrochloric acid, and the amount of acid present in said aqueous admixture is from about 10 to 25 weight percent based upon the total amount of water present in the reaction mixture.

6. The method of claim 1 wherein said acid is sulphuric acid, and the amount of acid present in said aqueous admixture is from about 30 to 60 weight percent based on the total amount of water present in the reaction mixture.

7. The method of claim 1 wherein the mole ratio of D-sorbitol to aromatic aldehyde is from about 1:1 to about 1:1.5.

8. The method of claim 1 wherein said purified, substantially dry di-acetal is even further purified by extracting it with a relatively non-polar solvent to remove tri-acetal impurities.

9. The method of claim 8, wherein said relatively non-polar solvent is selected from toluene and 1,1,1-trichloroethane.

10. A method for producing a di-acetal which comprises: admixing an effective amount of D-sorbitol into an aqueous solution of a mineral acid so as to form a resulting substantially homogeneous admixture containing a catalytic amount of said mineral acid; incrementally admixing an effective amount of an aromatic aldehyde into said homogeneous aqueous admixture at a rate sufficient to allow a substantially spontaneous reaction with said D-sorbitol so as to form an aqueous slurry containing crude di-acetal, said effective amount of aromatic aldehyde being that amount sufficient to provide a ratio of D-sorbitol to aromatic aldehyde of from about 1:.75 to about 1:1.75; separating said crude di-acetal from the liquid phase of the aqueous slurry; neutralizing the separated crude di-acetal with an aqueous alkaline admixture; washing the neutralized crude di-acetal with water to remove mono-acetal impurities present in said crude di-acetal; drying the washed di-acetal to remove substantially all of the residual water; and further purifying said dried di-acetal product by extracting it with a relatively non-polar solvent to remove tri-acetal impurities; and recovering a highly purified, substantially dry di-acetal product.

11. The method of claim 10 wherein said aromatic aldehyde is selected from benzaldehyde, ortho-, para- and meta-tolualdehyde, anisaldehyde and substituted benzaldehydes having 1 to 3 substituents in their benzene nucleus wherein said substituents are selected from lower alkyl having fewer than 5 carbon atoms, methoxy, mono- and di-alkylamino, nitro and halogen.

12. The process of claim 11, wherein said aromatic aldehyde is selected from benzaldehyde, meta- and para-tolualdehyde, meta- and para-chlorobenzaldehyde, and meta- and para-bromobenzaldehyde.

* * * * *

UNITED STATES PATENT AND TRADEMARK OFFICE
CERTIFICATE OF CORRECTION

PATENT NO. : 4,562,265

DATED : December 31, 1985

INVENTOR(S) : Greville Machell

It is certified that error appears in the above-identified patent and that said Letters Patent is hereby corrected as shown below:

Col. 2, line 53, "di-alkylasino" should be -- di-alkylamino--.

Col. 3, line 5, "alkaline" should be -- alkali --.

Col. 6, line 14, before the word "significant" add --A --.

Signed and Sealed this

Fourteenth Day of October, 1986

[SEAL]

Attest:

DONALD J. QUIGG

Attesting Officer

Commissioner of Patents and Trademarks